(12) United States Patent
Rydin et al.

(10) Patent No.: US 6,196,968 B1
(45) Date of Patent: Mar. 6, 2001

(54) DIRECT VISION SUBCUTANEOUS TISSUE RETRACTOR AND METHOD FOR USE

(75) Inventors: Jeffrey Rydin, Winnetka, IL (US); Thomas J. Palermo; Kenneth A Peartree, both of San Jose, CA (US)

(73) Assignee: General Surgical Innovations, Inc., Norwalk, CT (US)

( * ) Notice: Subject to any disclaimer, the term of this patent is extended or adjusted under 35 U.S.C. 154(b) by 0 days.

(21) Appl. No.: 09/150,909

(22) Filed: Sep. 10, 1998

Related U.S. Application Data

(63) Continuation-in-part of application No. 08/925,967, filed on Sep. 9, 1997, now Pat. No. 5,913,818, which is a continuation-in-part of application No. 08/867,133, filed on Jun. 2, 1997, now Pat. No. 6,033,361.

(51) Int. Cl.[7] ........................................................ A61B 1/32

(52) U.S. Cl. ........................... 600/210; 600/226; 600/227; 600/235; 600/245

(58) Field of Search .................................... 600/201, 205, 600/210, 212, 226, 227, 231, 235, 245, 190, 191, 197, 199; 606/190

(56) References Cited

U.S. PATENT DOCUMENTS

| | | |
|---|---|---|
| 518,842 | 3/1894 | Scheerer . |
| 659,182 | 10/1900 | Pilling . |
| 2,082,782 | 6/1937 | Allen . |
| 2,201,331 | 5/1940 | Wright . |
| 2,575,253 | 11/1951 | Bicek . |
| 2,653,597 | 9/1953 | Canan . |
| 2,812,758 | 11/1957 | Blumenscheia . |
| 2,829,649 | 4/1958 | Glemner . |
| 3,509,873 | 5/1970 | Karlin . |
| 3,570,475 | 3/1971 | Weinstein . |
| 3,638,644 | * 2/1972 | Reick .................................. 600/191 |

(List continued on next page.)

FOREIGN PATENT DOCUMENTS

| | | | |
|---|---|---|---|
| 2662929 | 12/1991 | (FR) . | |
| 375491 | * 6/1932 | (GB) | .................................... 600/197 |
| 2078526 | * 1/1982 | (GB) | .................................... 600/245 |
| 2133694 | * 8/1984 | (GB) | .................................... 600/245 |

OTHER PUBLICATIONS

P. 13, Fine Instruments and Video Systems for Endoscopic Plastic Surgery, Endoscopic Plastic Surgery, Snowden–Pencer USA (1994).

Brochure, Endoscopic Approach to Vein Harvesting Endoscopic Vein Harvest 1996. Ethicon Endo–Surgery, Inc.

Gary Chamberlan, "Bypass Surgery Made Easier", Jan. 6, 1997 Design News, pp. 57–62.

U.S. Surgical Corporation, "The Mini Harvest System for Minimally Invasive Saphenous Vein Harvesting", pp. 1–7. (No Date).

Cardiovascular Instrumentation, "SaphLITE Saphenous Vein System", Genzyme Surgical Products, pp. 1–4, (1998).

*Primary Examiner*—Jeffrey A. Smith

(57) ABSTRACT

A retractor includes an elongate member having an arcuate cross-section defining an elongate passage therein, and a handle molded to its proximal end. A transparent illumination member has a proximal portion connectable to a light source, and a distal portion that extends within the elongate passage along an inner surface of the elongate member, and includes a plurality of grooves for diffusing light transmitted from the proximal portion uniformly into and along the elongate passage. The device may also include a support member attachable to the proximal end of the elongate member to further facilitate visualization of and/or access into the elongate passage. The device may be inserted into an incision and advanced along a section of a tissue structure therein to hold open a working space above the tissue structure without external support A light source may be connected to the proximal portion of the illumination member, thereby transmitting light into the working space while a surgical procedure is performed therein.

22 Claims, 3 Drawing Sheets

U.S. PATENT DOCUMENTS

| | | |
|---|---|---|
| 3,651,800 | 3/1972 | Witbanks . |
| 3,851,642 * | 12/1974 | McDonald . |
| 4,232,660 | 11/1980 | Coles . |
| 4,380,999 | 4/1983 | Healy . |
| 4,562,832 | 1/1986 | Wilder et al. . |
| 4,686,972 | 8/1987 | Kurland . |
| 4,934,352 | 6/1990 | Sullivan, Jr. . |
| 5,667,480 | 9/1997 | Knight et al. . |
| 5,902,315 * | 5/1999 | DuBois .............................. 600/210 X |
| 5,913,818 * | 6/1999 | Co et al. ........................... 600/210 X |
| 5,922,004 * | 7/1999 | DuBois ................................ 606/190 |
| 6,033,361 * | 3/2000 | Co et al. .............................. 600/210 |

* cited by examiner

DIRECT VISION SUBCUTANEOUS TISSUE RETRACTOR AND METHOD FOR USE

This application is a continuation-in-part of application Ser. No. 08/925,967, (U.S. Pat. No. 5,913,818) filed Sep. 9, 1997, which is a continuation-in-part of application Ser. No. 08/867,133, (U.S. Pat. No. 6,033,361) filed Jun. 2, 1997 U.S. Pat. No. 6,033,361, the disclosures of which are expressly incorporated herein by reference.

FIELD OF THE INVENTION

The present invention relates generally to surgical retractors, and more particularly to vascular retractors that are self-supporting and/or provide an illuminated longitudinal working window for vascular harvesting procedures.

BACKGROUND OF THE INVENTION

Numerous surgical procedures, such as coronary bypass surgery, reverse or in-situ femoral-popliteal or femoral-tibial bypass procedures and the like, may involve accessing and/or harvesting the saphenous vein or other blood vessel of a patient. For example, in coronary bypass surgery, a vein may be harvested from elsewhere in the patient's body and grafted into place between the aorta and a coronary artery. It is generally preferred to use a vein taken from the patient undergoing the surgery, as the patient is a ready source of suitable veins that will not be rejected by the body after grafting. In particular, the saphenous vein in the leg is often used for this procedure, for example, because the saphenous vein is typically 3–5 mm in diameter and comparable in size to the coronary arteries. Furthermore, the venous system of the leg is sufficiently redundant that the saphenous vein may be removed and the remaining veins in the leg will continue to provide adequate return blood flow. Alternatively, the cephalic vein in the arm may sometimes be used.

Traditionally, to harvest the saphenous vein, an open surgical procedure has been used to expose and remove the vein from the leg. Because of wound morbidity and patient pain often encountered in such procedures, however, minimally invasive access has become increasingly preferred.

For example, instead of an open procedure, an interrupted incision method may be used in which a series of incisions with skin bridges between them are made between the groin, the knee and/or the ankle. Through the incisions, the surgeon dissects the vein from the surrounding tissues, lifts the vein from the tissues, and divides and ligates the various tributary veins that feed into the saphenous vein. Once the vein is completely mobilized, the surgeon cuts the ends of the vein and removes it from the leg. The incisions in the leg are closed, and the vein is prepared for implantation.

During an interrupted incision procedure, a retractor may be used to assist in visualization of the vein. The retractor typically includes a wide, flat shaft with a handle on its proximal end made from stainless steel. The retractor may be inserted into an incision and directed along a previously dissected path over a section of vein to be harvested. The handle of the retractor may then be lifted away from the surface of the leg, thereby maintaining the space created by dissection under the shaft adjacent the vein in an open condition. Such retractors may include a source of light connected to the proximal end, and light from the light source may be projected into the space to facilitate visualization of the vein.

In an alternative method, vein harvesting may be accomplished using an endoscopic procedure. One or more small incisions may be made at selected locations for providing access to the vein being harvested. For example, to harvest the saphenous vein, an incision may be made at the groin, at the knee, and/or at the ankle. A tunneling instrument, such as a blunt or soft-tipped dissector, may be utilized to dissect subcutaneous tissue along the anterior surface of the vein being harvested. Such instruments generally include an elongate member, which can be fabricated from transparent, opaque or other material, having a rounded distal end and a passage therein for receiving an endoscope, the endoscope providing visualization within or beyond the walls of the instrument.

The tunneling instrument is inserted into the incision and advanced or pushed along between tissue layers to dissect and expose the saphenous vein. The tip of the instrument is generally kept near or in contact with the vein as the instrument is advanced along, thereby creating a small tunnel adjacent the anterior surface of the vein. An inflatable balloon (alternatively provided in a collapsed condition on the tunneling instrument prior to insertion into the incision) may be introduced into the tunnel, and inflated to further dissect the tunnel to an appropriate size for surgery.

Once the desired length of vein is exposed and an appropriate tunnel developed, the balloon and/or tunneling instrument may be removed, and a retractor, typically a wide flat shaft with a handle on its proximal end, may be inserted into the incision and directed along the dissected path over the section of vein to be harvested. The handle of the retractor may then be lifted away from the surface of the leg, thereby maintaining the working space created by dissection under the shaft adjacent the vein in an open condition. Surgical instruments may then be inserted into the working space to dissect the tissues surrounding the vein, ligate tributary veins, and mobilize the vein. An endoscope may be provided in a passage in the retractor or inserted directly into the working space to allow visualization during the harvesting procedure.

Retractor devices in vein harvesting procedures often have limitations. For example, such retractors typically require external support to hold the retractor away from the surface of the vein and maintain the working space. The surgeon or physician's assistant may have to hold a handle on the retractor, preventing both hands from being free for the procedure or may even require an assistant. Alternatively, an external mechanical support may be provided to hold the retractor, but such a support may interfere with access to the operative site.

Some retractors include a distal hood capable of maintaining a working space thereunder. These hoods, however, only create a limited self-supported working space, requiring that the retractor be moved when it is desired to work in a new location. Such retractors also generally require external support to provide access along the retractor shaft between the incision and the hooded space.

Accordingly, there is a need for a device for retracting subcutaneous tissues and/or for holding open a working space during surgical procedures that provides improved illumination and/or visualization within the space.

SUMMARY OF THE INVENTION

The present invention is directed to vascular retractors that are self-supporting and/or provide an illuminated working space for vein harvesting or similar procedures. In one aspect of the present invention, a device for retraction of subcutaneous tissue is provided that includes an elongate member having proximal and distal ends, and having an arcuate cross-section defining an elongate passage therein.

The device also includes a substantially transparent illumination member or lightpipe having a proximal portion connectable to a source of light, and a distal portion within the elongate passage for directing light from the proximal portion into the elongate passage.

The elongate member is preferably formed from injection molded plastic, and, if desired, may be formed from a substantially transparent material for facilitating visualization beyond the walls of the elongate member. In a preferred form, the device also includes a handle extending from and preferably integrally molded to the proximal end of the elongate member. More preferably, the handle extends substantially perpendicularly to a longitudinal axis of the elongate member away from the elongate passage which may facilitate visualization of and/or access to the elongate passage.

The illumination member preferably extends along an inner surface of the elongate member and may include an illumination window directed towards the elongate passage. The distal portion of the illumination member and the inner surface of the elongate member may include cooperating tabs and slots for securing the distal portion of the illumination member to the inner surface. The proximal and distal portions of the illumination member are preferably integrally molded together from injection molded plastic to facilitate the passage of light from a light source at the proximal portion to the distal portion.

The illumination member preferably includes a plurality of lateral grooves in the distal portion, e.g., in an upper surface of the distal portion, for diffusing light transmitted from the proximal portion into the distal portion, e.g. through a lower surface of the distal portion towards a longitudinal working window defined by the elongate member. More preferably, the lateral grooves extend progressively deeper into the distal portion in the direction towards a distal tip of the illumination member for diffusing light substantially uniformly along the elongate passage and/or the longitudinal working window. Thus, an external source of light may be used to illuminate the longitudinal working window along the elongate passage to facilitate visualization of a blood vessel, such as the saphenous vein, or other subcutaneous tissue structure, during vein harvest or other procedures.

The device may also include a support member extending from the proximal end of the elongate member for facilitating access to and/or visualization of the elongate passage. The support member is preferably attachable to a handle or handle cover (described below) on the proximal end of the elongate member. In addition, the support member is preferably adjustable and extends substantially perpendicularly to a longitudinal axis of the elongate member towards the elongate passage when attached to the handle or handle cover of the elongate member. For example, in a preferred form, the support member and the proximal end of the elongate member and/or the handle may include a set of cooperating tabs and slots for detachably securing the support member to the elongate member in one of a plurality of available positions, thereby providing adjustability. For example, the support member may be attached to the elongate member at one of a plurality of incremental positions to raise the proximal end of the elongate member to a predetermined height and/or to further tent the entrance of an incision to facilitate visualization and/or access to the working space held open by the device through the incision.

In a preferred form, the support member includes a pair of arms defining an open space therebetween to straddle the access path to the elongate passage through the support member. The arms may be attached at their lower ends to a base, preferably having a slightly curved shape contoured to fit the surface of a patient's anatomy. The support member may facilitate use of the retraction device in a hands-free capacity, i.e., the support member may be sufficiently stable to support the elongate member on its own, thereby allowing a surgeon to use both hands during a vein harvesting or similar procedure.

In another aspect of the present invention, a device for retraction of subcutaneous tissue is provided that includes a retractor member having an elongate portion including proximal and distal ends, a handle extending from the proximal end of the retractor portion, and a substantially transparent illumination member having a proximal portion connectable to a source of light, an intermediate portion extending through the handle, and a distal portion extending along a lower surface of the elongate portion. The distal portion of the illumination member preferably includes a surface for directing light transmitted through the illumination member from a source of light connected to the proximal portion towards a working space held open by the device.

The handle includes a sleeve through which the proximal portion of the illumination member extends, which may include an adapter for attaching a source of light to the sleeve. The handle preferably includes a cavity through which the intermediate portion of the illumination member extends, and a handle cover attachable over the cavity.

To assemble the device, the proximal portion of the illumination member may be directed through the sleeve, while the distal portion of the illumination member is advanced along the lower surface of the elongate portion, until the intermediate portion enters the cavity in the handle. Preferably, the distal portion of the illumination member and the elongate portion include cooperating tabs and slots for substantially securing the distal portion to the lower surface of the elongate portion. The intermediate portion of the illumination member may substantially engage guide rails within the cavity to further secure the illumination member.

A handle cover may be placed over the cavity, and substantially secured to the handle, to thereby substantially enclose the cavity and/or to further secure the intermediate portion. The assembled device may then be packaged and provided to a surgeon or other user preassembled. A support member, such as that described above, may also be provided with the device for supporting the elongate portion of the device, as previously described.

The device may then be used in a method for retracting tissue to maintain a working space during a surgical procedure involving a subcutaneous tissue structure of a patient. An incision may be created at a location adjacent one end of the tissue structure, and a layer of tissue may be dissected above a section of the tissue structure through the incision. The retractor may be inserted into the incision, and advanced along the section of the tissue structure while being oriented. The retractor may hold open a longitudinal working space above the tissue structure and within the arcuate cross-section of the retractor. Preferably, the retractor is self-supporting and maintains the working space without external support. A source of light may be connected to the proximal portion of the illumination member, thereby transmitting light through the illumination member into the working space, and a surgical procedure may then be performed within the working space.

If desired, a second incision may be created adjacent to another length of the tissue structure, and the retractor used to hold open another working space, for example, to allow longer sections of the saphenous vein to be harvested for use in coronary bypass graft surgery. In addition, the support member may be attached to the proximal end of the device after being inserted into the incision, the support member holding the proximal end of the retractor at a predetermined height above the tissue structure to facilitate access into the working space through the incision.

Thus, the device may be used during a vein harvesting procedure to harvest a section of the saphenous vein through one or more incisions, each of which are preferably not more than about 4 cm long. The procedure may substantially reduce the wound morbidity and/or patient pain often associated with open harvesting procedures, while not requiring use of an endoscope and the more demanding surgical methods required for endoscopic surgery.

Additional objects and features of the present invention will become apparent from consideration of the following description taken in conjunction with the accompanying drawings.

DETAILED DESCRIPTION OF THE PREFERRED EMBODIMENTS

Figure 1:
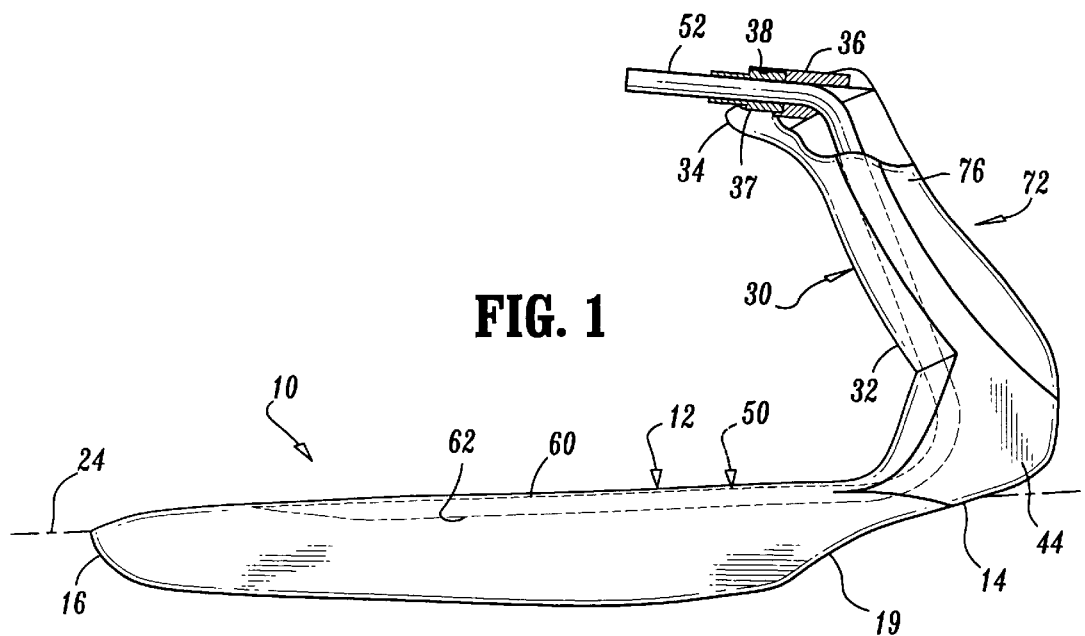
FIG. 1 is a side view of a first preferred embodiment of a retractor device in accordance with the present invention.
Figure 2:
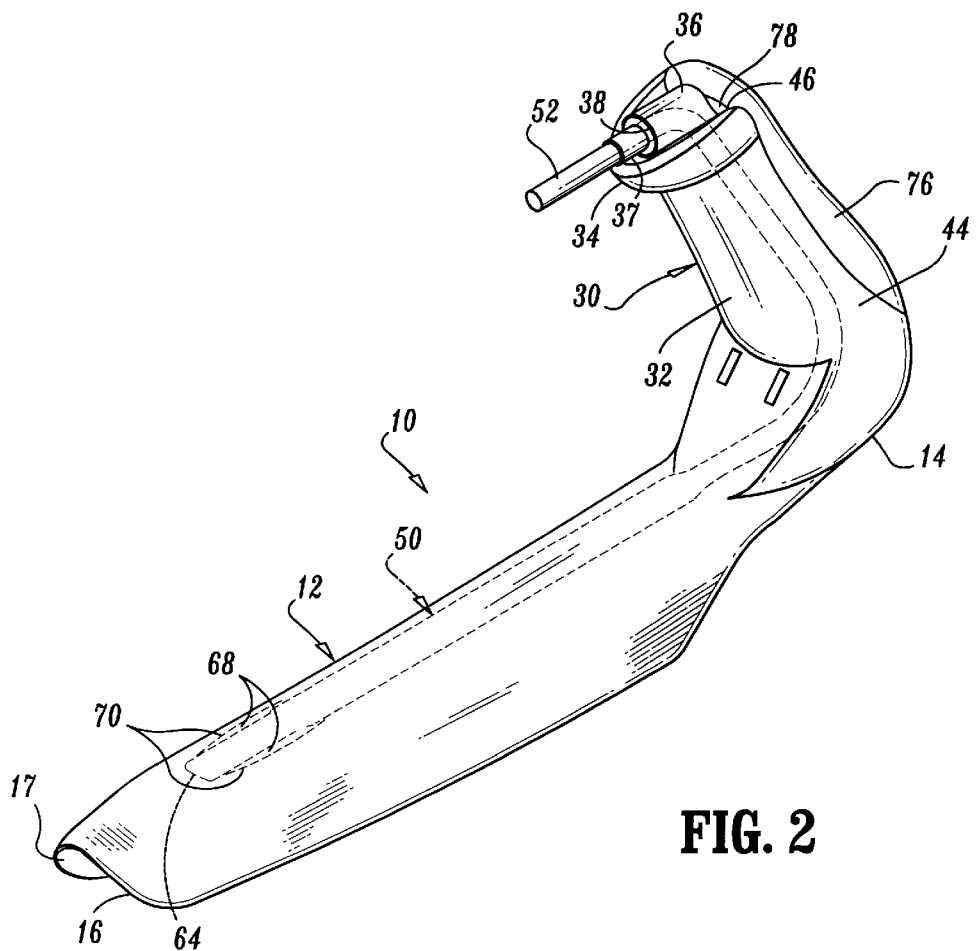
FIG. 2 is a perspective view of the retractor device of FIG. 1, including a lightpipe shown in phantom.

Turning now to the drawings, FIGS. 1–6 show a preferred embodiment of a retractor device 10 in accordance with one aspect of the present invention. The retractor device 10 includes an elongate member 12, a handle 30, a lightpipe 50, and a handle cover 72.

Figure 3A:
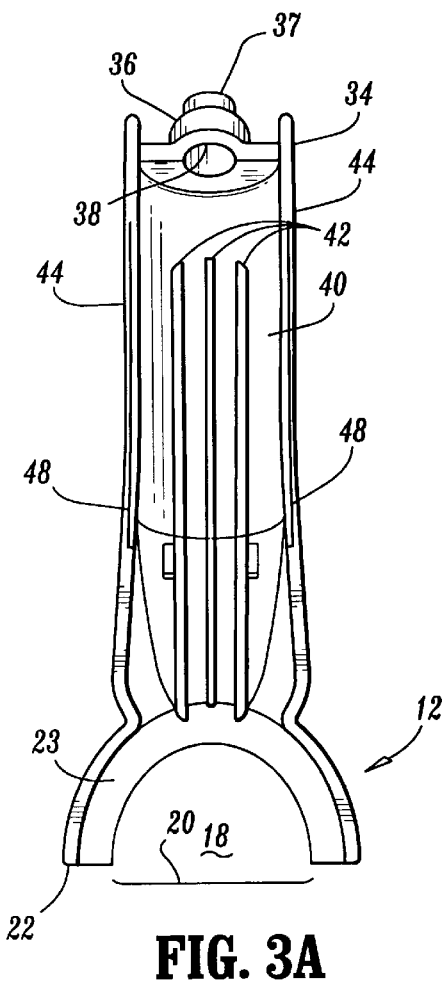
FIGS. 3A and 3B are back views of the retractor device of FIG. 1, with the handle cover removed and attached, respectively.
Figure 3B:
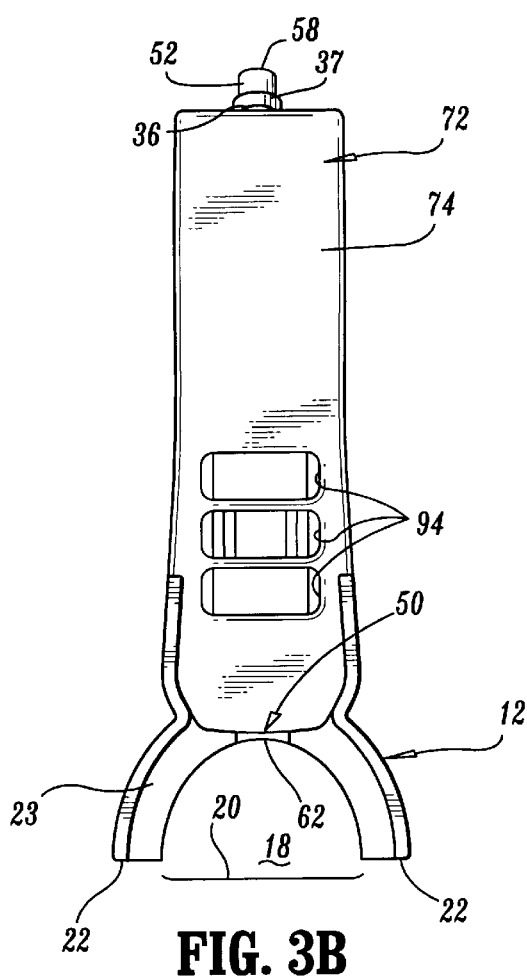

The elongate member 12 has a proximal end 14, a distal end 16, and an arcuate or "C" cross-section, as best seen in FIGS. 3A and 3B. The arcuate cross-section may define a portion of the periphery of a circle, an ellipse or similar shape. The distal end 16 is preferably rounded or streamlined to minimize tissue trauma when the retractor device 10 is directed along a dissected space in a patient (not shown), and may include a distal opening 17 to allow access beyond the distal end 16. The elongate member 12 defines an elongate passage 18 therein extending along a longitudinal axis 24 between the proximal and distal ends 14, 16. The elongate member 12 also defines a longitudinal working window 20 along the elongate passage 18 between longitudinal edges 22 of the elongate member 12.

The elongate member 12 may be fabricated from any suitable metal or plastic material, but preferably is formed from injection molded polymer, such as polycarbonate, or other engineering plastics. Alternatively, the elongate member may be formed in a manner which facilitates cleaning and/or of a semi-rigid material, such as polyetherimide, which may be suitable for sterilization and reuse. The material may also be substantially transparent to facilitate visualization beyond or through the walls of the elongate member 12.

The elongate member 12 may also include circumferentially extended edges or curved tabs (not shown) integrally formed along a portion of the edges 22 of the elongate member 12 and extending peripherally from the edges 22, thereby defining an extended periphery (not shown). The extended edges may increase the size of the working space held open by the retractor device 10 since the extended periphery further tents the working space, particularly at the location adjacent the extended edges. Additional discussion of such extended edges may be found in copending application Ser. No. 08/867,133, filed Jun. 2, 1997, now U.S. Pat. No. 6,033,361, the disclosure of which is expressly incorporated herein by reference.

The handle 30 is preferably integrally molded to and extends from the proximal end 14 of the elongate member 12, although alternatively the handle 30 may be provided as a separate component (not shown) attachable to the elongate member 12. The handle 30 preferably extends substantially perpendicularly to the longitudinal axis 24 away from the elongate passage 18, thereby facilitating manipulation of the retractor device 10 during a surgical procedure. The handle 30 includes a front surface 32 and side surfaces 44, preferably having a generally curved shape for facilitating grasping of the handle 32, and includes an upper end 34.

A cylindrical sleeve 36 is integrally molded to the upper end 34, including an aperture 38 communicating with a cavity 40 within the handle 30 defined by the front and side surfaces 32, 44. A universal cable adapter 37 may be attached to the cylindrical sleeve 36, for example, by insert-molding. The universal cable adapter 37 may be formed from aluminum or similar material, and may include threads for securing a similarly threaded light cable or other source of light (not shown) to the cylindrical sleeve 36. Alternatively, the adapter 37 may include other connectors for cooperatively mating with a light source.

The cavity 40 extends substantially between the upper end 34 of the handle 30 and the proximal end 14 of the elongate member 12. A plurality of guide rails 42 are integrally molded to the handle 30 within the cavity 40 and extend at least partially between the aperture 38 in the cylindrical sleeve 36 and the elongate passage 18 within the elongate member 12. The handle 30 may also include a pair of recesses 46 in the upper end 34 and elongate tabs 48 along the side surfaces 44 for cooperating with tabs 78 on the handle cover 72 to substantially secure the handle cover 72 to the handle 30, as described further below.

Figure 4:
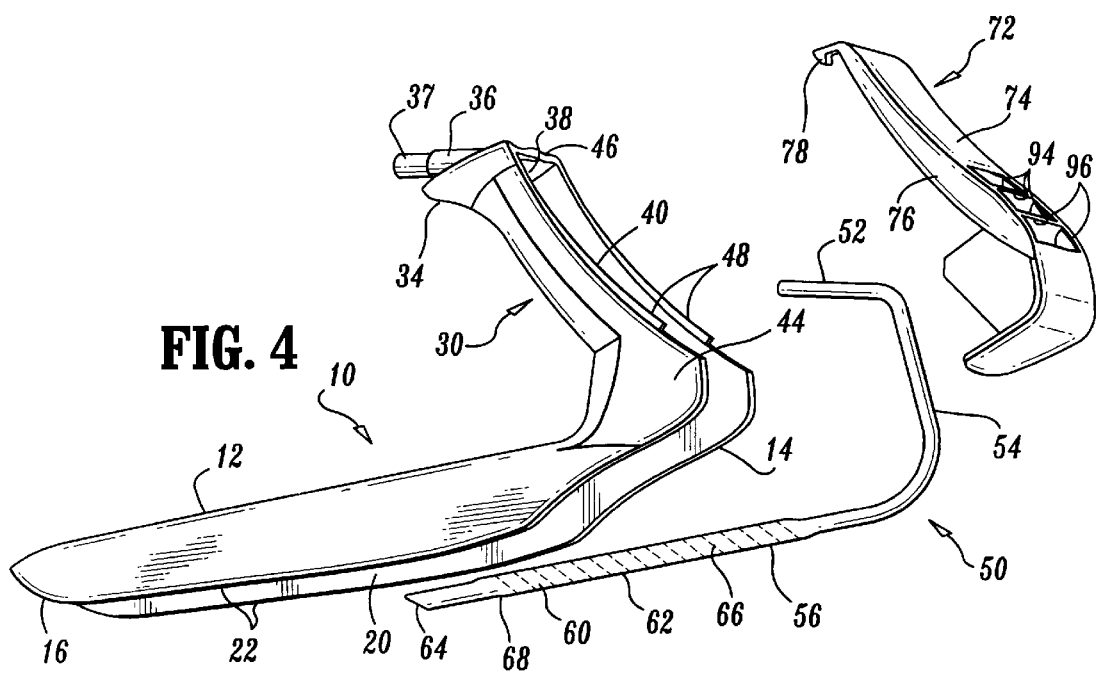
FIG. 4 is an exploded perspective view of the retractor device of FIG. 1
Figure 5:
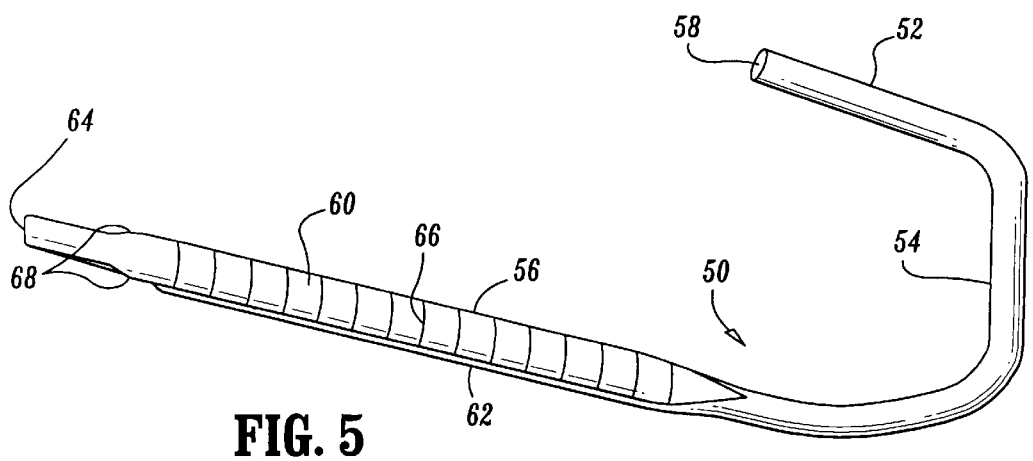
FIG. 5 is a perspective detail of a lightpipe for use with the retractor device of FIG. 1.

With particular reference to FIGS. 4 and 5, the lightpipe 50 is a substantially transparent illumination member, preferably formed from injection molded plastic that allows efficient transmission of light therethrough, such as polystyrene. The lightpipe 50 includes a proximal portion 52, a curved intermediate portion 54 and a distal portion 56, preferably integrally molded as a single piece to prevent substantial loss of light passing therethrough. The proximal and intermediate portions 52, 54 preferably have a substantially cylindrical shape to facilitate the transmission of light therethrough from a proximal end 58 of the lightpipe 50.

The distal portion 56 has a generally flat configuration defining an upper surface 60 and a lower surface 62, and terminates in a distal tip 64. Preferably, the upper surface 60 includes a plurality of lateral grooves 66 extending into the upper surface 60 for deflecting light passing along the distal portion 56 through the lower surface 62, as described further below. More preferably, the lateral grooves 66 extend substantially perpendicular to the longitudinal axis 24 and penetrate progressively deeper into the upper surface 60 of the distal portion 56 in the direction of the distal tip 64 to diffuse light essentially perpendicularly to and substantially uniformly along the longitudinal axis 24 within the elongate passage 18. The bottom of the lateral grooves 66 may be ramped at a predetermined angle, e.g., oblique with respect to the longitudinal axis 24, to further deflect light substantially perpendicularly to the longitudinal axis 24 towards the longitudinal working window 20.

In alternative forms, the distal portion 56 of the lightpipe 50 may be substantially cylindrical (not shown) and the lateral grooves 66 may be provided on the upper half of the distal portion 56 and/or on the lower half of the distal portion 56 (not shown). In a further alternative, the lateral grooves 66 may be spaced progressively closer together in the direction of the distal tip 64 (not shown) to further facilitate substantially uniform diffusion of light from the distal portion 56.

The distal portion 56 also includes a pair of ramped tabs 68 proximate the distal tip 64 for cooperatively engaging slots 70 formed on an inside surface 23 of the elongate member 12 for substantially securing the distal portion 56 of the lightpipe 50 to the elongate member 12. To attach the lightpipe 50 to the elongate member 12, the proximal portion 52 of the lightpipe 50 is directed through the aperture 38 in the handle 30 until the intermediate portion 54 substantially engages the guide rails 42 in the cavity 40. Simultaneously, the distal portion 56 is directed along the inside surface 23 of the elongate member 12 until the ramped tabs 68 substantially engage the slots 70.

With particular reference to FIGS. 3B and 4, the handle cover 72 may then be attached to the handle 30 to substantially enclose the cavity 40 and/or to further substantially secure the lightpipe 50 therein. The handle cover 72 includes a back surface 74 and side surfaces 76 having a configuration complementary to the configuration of the handle 30. The handle cover 72 includes tabs 78 adapted to be received in the recesses 46 in the upper end 34 of the handle 30 such that the handle cover 72 may be attached thereby to the handle 30. Preferably, when the handle cover 72 is received on the handle 30, the elongate tabs 48 on the handle 30 substantially engage the side walls 76 of the handle cover 72 to further secure the handle cover 72 onto the handle 30. The cooperating tabs 78 and recesses 46 and the elongate tabs 48 may substantially secure the handle cover 72 onto the handle 30 such that adhesives may be unnecessary.

For a reusable version of the retractor device 10, the elongate member 12, the lightpipe 50 and the handle cover 72 may be capable of disassembly for cleaning and/or sterilization. Alternatively, in a single use version, the elongate member 12, the lightpipe 50 and handle cover 72 may be substantially permanently attached together prior to packaging, thereby providing a ready-to-use device. For such a single use version, the handle cover 72 may be bonded to the handle 30 using adhesives and the like, either alone or in conjunction with cooperating tabs and recesses.

During a procedure, a light cable or other source of light (not shown) may be coupled to the proximal portion 52 of the lightpipe 50, preferably to the universal cable adapter 37, such that light is directed into the proximal end 58 of the lightpipe 50. Light from the light cable then passes through the proximal and intermediate portions 52, 54 and enters the distal portion 56. As the light travels towards the distal tip 64 of the distal portion 56, the light encounters the lateral grooves 66, which deflect the light through the lower surface 62. The depth of the lateral grooves 66 into the upper surface 60 may be selectively altered to vary illumination along the distal portion 56 of the lightpipe 50. Thus, light may be diffused in any preferred manner through the lower surface 62 along the distal portion 56.

The handle 30 of the retractor device 10 may be grasped in one hand, and the elongate member 12 inserted into an incision leading to a dissected space, for example, a transverse or longitudinal incision about 4 cm long, to retract subcutaneous tissue to hold open a dissected anatomic space therein. Once the elongate member 12 is positioned within the space, for example, along a vein being harvested, the lightpipe 50 transmits light into the space, and particularly to the operating area within the longitudinal working window 20 of the elongate member 12. The distal portion 56 of the lightpipe 50 preferably diffuses the light substantially uniformly along the longitudinal axis 24, thereby facilitating visualization of the vein and/or branches for easy ligation and removal.

Figure 6:
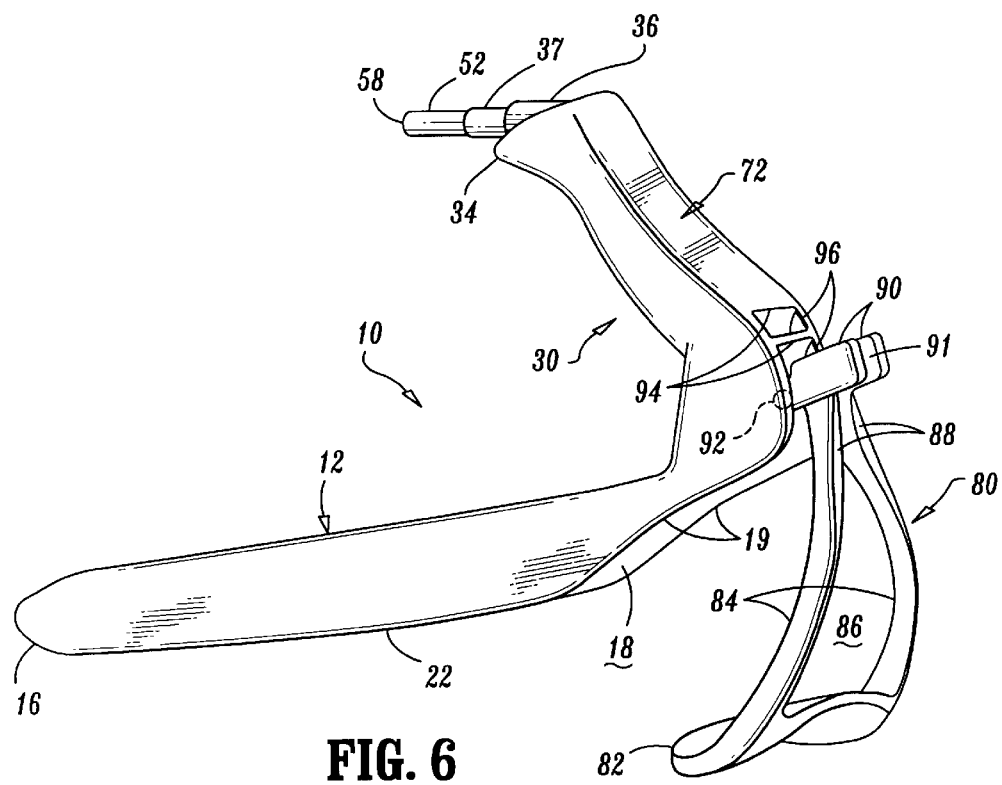
FIG. 6 is a perspective view of an alternative embodiment of the retractor device of FIG. 1, including an adjustable auxiliary support member attached to a handle of the retractor device.

In addition, as shown in FIG. 6, the retractor device 10 may include an auxiliary support member or stand 80 for elevating the proximal end 14 of the retractor device 10. The support member 80 includes a base 82 and a pair of legs 84 that are preferably integrally molded together. The base 82 preferably has a slightly curved shape contoured to fit the surface of a patient's anatomy, and the pair of legs 84 preferably extend from opposite sides of the base 82 towards one another to define a substantially triangular open space 86, facilitating access to the elongate passage 18.

Upper ends 88 of the legs 84 are disposed in close proximity to one another, and include tabs 90 adjacent one another that define a gap 91 therebetween. A hub 92 extends from an outer surface of each tab 90, i.e., opposite the gap 91. Preferably, the legs 82 are semi-rigid, i.e., are sufficiently rigid to support the retractor device 10, but are sufficiently flexible that the tabs 90 may be compressed towards one another, but resiliently return to define the narrow gap 91.

The handle cover 72 includes a plurality of transverse slots 94 having a width similar to the uncompressed spacing of the tabs 90 such that the tabs 90 may be received in an individual transverse slot 94. The transverse slots 94 also include a pair of recesses 96 therein for receiving the hubs 92. To attach the support member 80 to the retractor device 10, the tabs 90 are directed towards one another, i.e., reducing the width of the gap 91 between them, and then inserted into a selected transverse slot 94 in the handle cover 30, the compressed profile providing clearance for the hubs 92 to enter the transverse slot 94. The tabs 90 may then be released, the legs 84 resiliently returning the tabs 90 toward the uncompressed profile, apart from one another until the hubs 92 engage the recesses 96. Thus, the proximal end 14 of the retractor device 10 may be adjusted to a predetermined height above the surface of a patient's leg simply by moving the tabs 90 of the support member 80 to a corresponding transverse slot 94 in the handle cover 72.

With the support member 80 in place at a predetermined height, the proximal end 14 of the elongate member 12 may be raised to facilitate the performance of a surgical procedure within the elongate passage 18. For example, the open space 86 may facilitate visualization within the elongate passage 18. In addition, the support member 80 may facilitate the direction of surgical instruments (not shown) through the open space 86 and into the elongate passage 18. The support member 80 may also provide hands-free retraction, enabling a surgeon to use both hands during the procedure. In addition to the support member 80, the elongate member 12 may include recessed portions 19 adjacent the proximal end 14 to provide an enlarged entrance into the elongate passage 18, for example, to further facilitate visualization and/or the direction of surgical instruments into the elongate passage 18.

Alternatively, other adjustment mechanisms may also be provided that may, for example, be attachable or permanently fixed to the proximal end 14. The adjustment mechanism may fix the proximal end 14 at one of a plurality of heights to tent the incision and/or to facilitate access to the working space. For example, a raised frame (not shown) may be attachable to the patient's anatomy, such as by a strap around their leg, to which the proximal end 14 may be attached. The frame should include an open space therethrough to facilitate the introduction of surgical instruments into the elongate passage 18.

An important feature of a retractor device in accordance with the present invention is the arcuate cross-section which enables the device to retract and maintain subcutaneous tissue and hold open a working space during a surgical procedure. Conventional methods may be used to incise and dissect to create a subcutaneous space initially, for example, in preparation for vein harvesting from a patient's leg. Alternatively, U.S. Pat. No. 5,601,581, issued to Fogarty et al., discloses an apparatus and method suitable for dissecting a subcutaneous space. The disclosure of this reference and any others cited therein are expressly incorporated herein by reference.

To summarize such a useful procedure, a section of a tissue structure, for example a nerve or vein, especially the saphenous vein, may be selected to be harvested. An incision may be created at a location adjacent to one end of the selected structure, such as at the groin or knee. A tunneling instrument, such as a blunt or soft-tipped dissector, possibly including an inflatable balloon thereon, may be inserted into the incision and advanced along between tissue layers to identify the selected tissue structure. The tunneling instrument may be advanced along the anterior surface of the tissue structure and/or a balloon on the tunneling instrument may be inflated to create a dissected space of a desired size. Once the desired dissected space is developed, the balloon may be deflated, and the tunneling instrument may be removed from the dissected space through the incision.

A retractor in accordance with the present invention may then be inserted into the incision and directed along the dissected space while orienting the open side of the "C" shaped cross-section, e.g., the longitudinal working window 20, towards the tissue structure to hold open a working space above the tissue structure. The lightpipe 50 provides illumination within the working space and, in particular, facilitates visualization of a surgical site along the tissue structure within the working window 20. The arcuate shape of the retractor device 10 allows the subcutaneous tissues anterior to the surgical site, such as the tissues anterior to the saphenous vein, to be held up and away from the surgical site without needing external support. The longitudinal edges 22 of the retractor device 10 abut the subcutaneous tissues adjacent the anterior surface of the tissue structure, and the longitudinal working window 20 facilitates access along a desired length of the tissue structure, for example, of a vein being harvested. Surgical instruments may be introduced into the incision and directed along the working space to any point along the length of the longitudinal working window 20 without having to relocate the retractor device during a surgical procedure, such as a vein harvesting procedure.

If desired, a second incision may be created and the procedure repeated at another location on the patient's leg adjacent to the first incision, the retractor device holding open a second working space to facilitate additional tissue structure to be ligated and/or harvested. Thus, a retractor device 10 in accordance with the present invention may allow a relatively long section of a vein, nerve or other tissue structure to be harvested through a series of relatively small incisions spaced apart from one another.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. A device for retraction of subcutaneous tissue to hold open a working space within a patient's body, comprising:
   an elongate member having proximal and distal ends, and having an arcuate cross-section defining an elongate passage therein; and
   a substantially transparent illumination member having a proximal portion connectable to a source of light, and a distal portion within the elongate passage for directing light from the proximal portion into the elongate passage,
   wherein the illumination member includes a plurality of lateral grooves in the distal portion for diffusing light transmitted from the proximal portion into the distal portion towards a longitudinal working window defined by the elongate member,
   wherein the lateral grooves extend progressively deeper into the distal portion towards a distal tip of the illumination member for diffusing light substantially uniformly along the longitudinal working window.

2. A device for retraction of subcutaneous tissue to hold open a working space within a patient's body, comprising:
   an elongate member having proximal and distal ends, and having an arcuate cross-section defining an elongate passage therein;
   a substantially transparent illumination member having a proximal portion connectable to a source of light, and a distal portion within the elongate passage for directing light from the proximal portion into the elongate passage; and
   a support member extending from the proximal end of the elongate member for facilitating access to the elongate passage.

3. The device of claim 2, wherein the support member extends substantially perpendicularly to a longitudinal axis of the elongate member towards the elongate passage.

4. The device of claim 2, where in the support member is adjustable with respect to the proximal end of the elongate member.

5. The device of claim 2, wherein the support member and the proximal end of the elongate member include a plurality of cooperating tabs and slots for detachably securing the support member to the proximal end in one of a plurality of positions with respect to one another.

6. The device of claim 5, wherein the support member includes a pair of arms defining an open space therebetween for accessing the elongate passage through the support member.

7. A device for retraction of subcutaneous tissue to hold open a working space within a patient's body, comprising:

an elongate member having proximal and distal ends, and having an arcuate cross-section defining an elongate passage therein;

a substantially transparent illumination member having a proximal portion connectable to a source of light, and a distal portion within the elongate passage for directing light from the proximal portion into the elongate passage; and an adjustment mechanism on the proximal end of the elongate member for fixing the proximal end at one of a plurality of heights.

8. A device for retraction of subcutaneous tissue to hold open a working space within a patient's body, comprising:

a retractor member having an elongate portion including proximal and distal ends, and a handle extending from the proximal end of the elongate portion, the elongate portion having a substantially arcuate cross-section; and a substantially transparent illumination member having a proximal portion connectable to a source of light, an intermediate portion extending through the handle, and a distal portion extending along a lower surface of the elongate portion, the distal portion including a surface for directing light from a source of light connected to the proximal portion therethrough.

9. The device of claim 8, wherein the arcuate cross-section of the elongate portion defines an elongate passage therein, and wherein the distal portion of the illumination member extends along the elongate passage.

10. The device of claim 8, wherein the handle comprises a sleeve through which the proximal portion of the illumination member extends.

11. The device of claim 10, further comprising an adapter for attaching a source of light to the sleeve.

12. The device of claim 8, wherein the elongate portion and the handle are integrally molded together from molded plastic.

13. The device of claim 8, wherein the proximal, intermediate and distal portions of the illumination member are integrally molded together from molded plastic.

14. The device of claim 8, wherein the handle includes a cavity through which the intermediate portion of the illumination member extends.

15. The device of claim 14, further comprising a handle cover attachable to the handle for substantially enclosing the cavity.

16. A device for retraction of subcutaneous tissue to hold open a working space within a patient's body, comprising:

a retractor member having an elongate portion including proximal and distal ends, and a handle extending from the proximal end of the elongate portion; and a substantially transparent illumination member having a proximal portion connectable to a source of light, an intermediate portion extending through the handle, and a distal portion extending along a lower surface of the elongate portion, the distal portion including a surface for directing light from a source of light connected to the proximal portion therethrough, wherein the lower surface of the illumination member comprises a substantially flat surface oriented away from the lower surface of the elongate portion.

17. The device of claim 16, wherein the distal portion of the substantially flat surface includes a plurality of lateral grooves for diffusing light through the illumination window.

18. The device of claim 17, wherein the plurality of lateral grooves extend progressively deeper into the distal portion of the illumination member away from the proximal portion.

19. The device of claim 17, wherein the plurality of lateral grooves are in an upper surface of the distal portion of the illumination member.

20. A device for retraction of subcutaneous tissue to hold open a working space within a patient's body, comprising:

a retractor member having an elongate portion including proximal and distal ends, and a handle extending from the proximal end of the elongate portion; and a substantially transparent illumination member having a proximal portion connectable to a source of light, an intermediate portion extending through the handle, and a distal portion extending along a lower surface of the elongate portion, the distal portion including a surface for directing light from a source of light connected to the proximal portion therethrough; and an adjustment mechanism proximate the proximal end of the elongate portion for fixing the proximal end at one of a plurality of predetermined heights.

21. The device of claim 20, wherein the adjustment mechanism comprises a support member that is attachable to the handle of the retractor member by a plurality of cooperating tabs and slots.

22. A method for holding open a working space during a surgical procedure involving a subcutaneous tissue structure of a patient using a retractor having an arcuate cross-section defining a longitudinal working window and having a substantially transparent illumination member thereon including a proximal portion connectable to a source of light and a distal portion above the longitudinal working window, the method comprising the steps of:

creating an incision at a location adjacent one end of the tissue structure;

dissecting a layer of tissue above a section of the tissue structure through the incision;

inserting the retractor into the incision;

advancing the retractor along the section of the tissue structure while orienting the longitudinal working window towards the section of the tissue structure, the arcuate cross-section of the retractor holding open a working space above the section of the tissue structure without external support;

connecting a source of light to the proximal portion of the illumination member, thereby transmitting light through the illumination member into the working space;

attaching a support member to a proximal end of the retractor after the retractor is inserted into the incision, the support member holding the proximal end of the retractor at a predetermined height above the tissue structure to facilitate access into the working space through the incision; and performing a surgical procedure within the working space, wherein the distal portion of the illumination member includes a plurality of lateral grooves therein, and wherein the light transmitted through the illumination member is deflected by the plurality of lateral grooves towards the longitudinal working window, the plurality of lateral grooves diffusing the light substantially uniformly along the longitudinal working window, wherein the support member includes a base contoured to conform to the anatomy of the patient, and includes an open space therethrough for accessing the working space.

* * * * *